(12) United States Patent
Kilgarlin (10) Patent No.: US 11,887,733 B2
(45) Date of Patent: Jan. 30, 2024

(54) METHOD FOR PROVIDING SEMI-QUANTITATIVE TEST RESULTS FOR DRUG TEST STRIPS USING MACHINE LEARNING

(71) Applicant: Ronald Kilgarlin, Shreveport, LA (US)

(72) Inventor: Ronald Kilgarlin, Shreveport, LA (US)

(*) Notice: Subject to any disclaimer, the term of this patent is extended or adjusted under 35 U.S.C. 154(b) by 421 days.

(21) Appl. No.: 17/161,443

(22) Filed: Jan. 28, 2021

(65) Prior Publication Data

US 2022/0238224 A1    Jul. 28, 2022

(51) Int. Cl.
| | | |
|---|---|---|
| *G16H 50/20* | (2018.01) | |
| *G01N 21/78* | (2006.01) | |
| *G01N 33/487* | (2006.01) | |
| *G06T 7/00* | (2017.01) | |
| *G16H 30/40* | (2018.01) | |
| *G16H 10/40* | (2018.01) | |
| *G01N 21/77* | (2006.01) | |

(52) U.S. Cl.
CPC .............. *G16H 50/20* (2018.01); *G01N 21/78* (2013.01); *G01N 33/487* (2013.01); *G06T 7/0014* (2013.01); *G16H 10/40* (2018.01); *G16H 30/40* (2018.01); *G01N 2021/7759* (2013.01); *G06T 2207/20081* (2013.01); *G06T 2207/30004* (2013.01)

(58) Field of Classification Search
CPC ........ G16H 50/20; G16H 10/40; G16H 30/40; G01N 21/78; G01N 33/487; G01N 2021/7759; G06T 7/0014; G06T 2207/20081; G06T 2207/30004
See application file for complete search history.

(56) References Cited

U.S. PATENT DOCUMENTS

| | | | |
|---|---|---|---|
| 9,311,520 B2 | 4/2016 | Burg et al. | |
| 11,295,859 B2* | 4/2022 | Pulitzer | G06T 7/10 |
| 11,347,000 B2* | 5/2022 | Ozcan | G02B 6/06 |
| 2019/0343386 A1* | 11/2019 | Pulitzer | G16H 50/20 |

* cited by examiner

*Primary Examiner* — Wednel Cadeau (57) ABSTRACT

A system and method for evaluating the concentration of an analyte contained on a diagnostic device. The method includes preparing a database of a plurality of digital images of drug test strips showing different concentrations of analytes; preparing a machine learning model of the drug test strips; comparing an active diagnostic device to the machine learning model, and evaluating the concentration of analytes In the active diagnostic device by comparing the active diagnostic device drug panel to the drug panel of the machine learning model of a diagnostic device.

3 Claims, 8 Drawing Sheets

METHOD FOR PROVIDING SEMI-QUANTITATIVE TEST RESULTS FOR DRUG TEST STRIPS USING MACHINE LEARNING

FIELD OF THE INVENTION

The present invention is related to systems and methods for interpreting the concentration of biological materials contained in a drug test strip. Particularly, the present invention is related to system and methods for providing semi-quantitative test results for drug test strips using machine learning.

BACKGROUND OF THE INVENTION

"Drug testing" is performed to determine if a particular drug is present in a sample or is present in the sample in sufficient concentration. The sample tested may be, for example, urine, blood, or saliva. The form of testing done depends on how much information the tester needs about the concentration level of the drug in the sample.

For example, qualitative testing can be used if it is desirable to know whether the concentration of a drug is above a predetermined concentration level ("cut-off concentration"). Qualitative drug testing is typically performed at a collection facility using, for example, various on-site sample collection methods. Typical collection methods include urine cups, drug test strips, oral swabs, drug test sticks configured to collect and saliva stick, or the lock.

Since qualitative drug testing focuses on whether the drug is above the cut-off concentration level, the results of qualitative drug testing are reported as either Positive or Negative. As used with respect to qualitative testing, a positive result means that the drug is in the sample in concentration levels higher than the cut-off concentration. A negative result means that the concentration of the drug tested for is below the cut-off concentration.

It is well known to use drug testing strips ("pads") in conjunction with the drug testing collection device when testing for the presence of a specific drug or class of drugs. Drug test strips used in drug testing have been impregnated with biochemical reagents that respond to the presence of drugs from a specific drug class. When there is sufficient concentration of drugs from the class present, the drug test strip will change color to indicate the presence of the drug in the sample.

More specifically, it is well known that each test strip contains reagents that change color when exposed to an analyte solution. Each drug testing strip will typically include reagent pads for detecting or measuring analytes present in a biological sample such as urine or saliva. It is also well known that test strips may be used to test for analytes customarily found in the human body. For example, certain test strips that may test for glucose, bilirubin, ketones, specific gravity, blood, pH, protein, urobilirubin, nitrate, leukocytes, microalbumin, creatine, or the like.

Typical examples of a conventional method for collecting a sample to be tested includes a drug testing urine cup, or saliva stick (e.g., "diagnostic device"). Conventional diagnostic devices may incorporate one or more drug testing strips in its construction. A diagnostic device may include several test strips for testing for the presence of multiple drugs. The drug panels may appear as optically visible spaced lines. Such diagnostic devices may include a portion having spatially separated optically detectable signal (SSOSD) test strips, where each spatially separated test strip is configured to test for a different distinct analyte.

A SSOSD test strip may be configured to report the drug test results as optically detectable signals (e.g. immunoassay lines) indicating the presence, absence or relative levels of the various analytes. During use, a diagnostic device including a drug test panel (e.g., multiple drug test strips) may be placed in contact with a sample, such as a biological sample, to determine the presence of a drug in the sample. The drug test strips are comprised of absorbent material. A portion of the sample to be tested is partially absorbed by the drug test strips, typically through capillary action. If the analytes for which one of the test strip is design to detect are present, the test strip will react with drug-specific antibodies and give an optical indication of the drug's presence. In a typical example, the optical indication is visible as a change in color of the test strip.

In qualitative drug testing, the diagnostic device may include multiple test strips (i.e., "T line(s)") configured to changed colors to indicate the presence of a drug for which the test strip is testing.

For example, in a "positive" test result, the T Line disappears only if the concentration of analytes is above the cut-off concentration level. Contrarily, if the T-line shows any visible color, then the result of the drug test is Negative. A negative result means that the drug concentrations in the sample are below the cut-off concentration levels for a particular drug tested being tested.

In most cases, results received from the diagnostic device must be confirmed. The diagnostic device test panel may include a control line ("C" line) for use in confirming if the drug test strip is giving an accurate result. The C line may be used as a quality control technique to ensure, for example, that the test strip has not expired, or that the proper testing procedure has been followed.

The C line may be represented by a visible line on the drug strip. If the control line disappears when placed in contact with the sample, then the drug test strip results are deemed unreliable. If the result of the drug test is that the "C" line is visible and the "T" line is also visible then the drug test's negative is validated. However, if the "C" line is visible and the T line disappears, then the test's Positive result is validated. On the other hand, if the C Line disappears, then the test results are invalid no matter whether the T Line is visible or not.

In some case, such as for example where the tester is required to determine the concentration of drugs in a sample, the tester may prefer semi-quantitative testing over qualitative testing. Semi-quantitative drug testing is typically performed on a biological sample using an auto-analyzer such as those typically found in the clinic, hospital and toxicology laboratories. Semi-quantitative testing is ordinarily not done on the testing site. Instead, the sample is delivered to the testing facility for processing.

As with qualitative drug testing, semi-quantitative drug testing uses biochemical reagents that respond to the presence of drugs from a specific class. However, while results of the qualitative test depend on the concentration of the analytes relative to the cut-off level for the specific drug, the results of a semi-quantitative drug test are reported as numerical results representative of the concentration levels of the analyte in the sample being tested. In some instances, the numerical result from the semi-quantitative test represents the summed concentrations from all drugs in the class that contribute to the response. For instance, the numerical result generated by the semi-quantitative test for opiates customarily includes the summed contributions from morphine, codeine, hydrocodone, hydromorphone, and to a lesser extent, oxycodone and oxymorphone.

Like as what was described with respect to qualitative testing, the test strips change to indicate the presence of a particular drug. The magnitude of the color change is proportional to analyte concentration in the sample being tested. For example, the higher the concentration of the analyte in the sample, the more drastic the change in color. That is, in a typical example, the more concentration of the analyte in the sample, the more luminous the color of the test strip.

The advantage of conventional qualitative testing over semi-quantitative testing is that qualitative test results may be interpreted in real-time at the testing site. On the other hand, the semi-quantitative testing gives more information about the sample, such as, the concentration of the analyte. Unfortunately, the downside to semi-quantitative testing is that semi-quantitative tests must be read in a lab, hospital or other facility typically removed from the collection site. As such, semi-quantitative test results are not read in real-time.

What is needed is a system and method to interpret semi-quantitative test at the collection site in real-time.

SUMMARY OF THE INVENTION

The present invention teaches improvements not found in the prior art. The invention teaches a computer-enabled system and method for providing semi-quantitative test results for drug test strips using machine learning. The invention teaches a computer-enabled system and method for providing semi-quantitative test results in real-time, on the collection site.

In one exemplary embodiment of the invention, a computer-enabled application for determining the concentration of analytes in a biological sample is configured to be managed by a hand-held computing device. In a preferred embodiment, the computing device is a photonic enabled device. An example of a photonic enabled computing device would be a camera enable mobile phone, iphone or tablet. In such case, the camera will be enabled to take a picture of a drug strip color indication.

In another embodiment of the invention, the computer application is configured to receive the color indication data (e.g., digital image) from the photonic enabled device and translate the color indication data into a semi-quantitative result. In one aspect, results of the computer application may include a numerical result that represents the concentration level of drugs in the biological sample.

In yet another embodiment of the invention, the present invention teaches a drug screening system which includes a stand for holding the photonic enabled device. The diagnostic device which has been placed in contact with a biological sample to be tested, may be fitted in the stand. In a particular embodiment, the stand may be configured to position the photonic device's camera, facing the diagnostic device. In this way, the stand ensures that the distance of the diagnostic device from the photonic device may be consistent from one test to another.

In one exemplary embodiment, a machine learning model of reference diagnostic devices is used to determine which testing control variables are used to evaluate a drug test strip. In one aspect, a database of multiple machine learning models is generated using a plurality of digital images of reference diagnostic devices. One or more of the diagnostic devices may be "related." Related diagnostic devices as used herein are those diagnostic devices that require the same control variables to interpret them. In one aspect, groups of related diagnostic devices serve as a machine learning data set to generate the machine learning models for each group of related diagnostic devices.

In another exemplary embodiment, the present invention the machine learning model of related diagnostic devices includes generating a machine learning model of the drug strip panels corresponding to each of the machine models of reference diagnostic devices. In one aspect, the drug strip panels corresponding to the diagnostic devices used as machine learning data sets are used as the machine learning data set for generating the drug strip panel machine learning models.

In another aspect, the machine learning model of drug strip panels is segregated into a grid of images, wherein at least one of the modules of the grid of images includes control variables for use in evaluating an active diagnostic device.

In still another exemplary embodiment of the invention, a digital image of an active diagnostic device is captured by a photonic enabled device. An active diagnostic device is one that has been placed in contact with a biological fluid to be tested. In one aspect, the digital image of the active diagnostic device is used to select at least one of the machine learning model of diagnostic devices. The machine model of the drug panel corresponding to the selected machine learning model of diagnostic devices is used to select the machine learning model of drug strip panel to be used to evaluate the active diagnostic device.

In still another exemplary embodiment of the invention, a diagnostic device identifier for the active diagnostic device is used to select the machine learning model of diagnostic devices to be evaluated.

The present invention is designed for use interpreting single or multiple drug test strips. Typical bodily fluids tested by the invention include those used to test urine or saliva, including drug test strips designed for use with urine cups, urine dip cards, saliva box, saliva tube, saliva stick.

DETAILED DESCRIPTION OF EXEMPLARY EMBODIMENTS OF THE PRESENT INVENTION

This disclosure is set forth in the context of representative embodiments that are not to be otherwise limiting in any way.

The things and methods described herein should not be construed as being limiting in any way. Instead, this disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed things and methods require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged, omitted, or performed concurrently. Moreover, for the sake of simplicity, the attached figures may not show the various ways in which the disclosed things and methods can be used in conjunction with other things and methods.

Additionally, the description sometimes uses terms like "produce," "generate," "select," "capture," and "provide" to describe the disclosed methods. These terms are high-level abstractions of the actual operations that are performed. The actual operations that correspond to these terms can vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" encompasses mechanical, electrical, magnetic, optical, and physical, as well as other practical ways of coupling or linking items together, and does not exclude the presence of intermediate elements between the coupled items.

Any of the disclosed methods can be implemented as computer-executable instructions stored on one or more computer-readable storage media (e.g., non-transitory computer-readable media, such as one or more volatile memory components (such as DRAM or SRAM), or nonvolatile memory components (such as hard drives)) and executed on a computer (e.g., any commercially available computer, including smartphones or other mobile devices that include computing hardware). Any of the computer-executable instructions for implementing the disclosed techniques as well as any data created and used during implementation of the disclosed embodiments can be stored on one or more computer-readable media (e.g., non-transitory computer-readable media).

Consequently, when the present invention describes various data, such as codes, identifiers, or the like, it is understood that the data is stored in the computer-readable storage media and the data may be manipulated, retrieved, or otherwise operated on by the processors described herein.

Where the invention discusses a method step or process, it is to be understood that the method step or process may be implemented with computer-executable instructions. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, HTML5, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Theories of operation, scientific principles or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

In the following description, certain terms may be used such as "up," "down," "upper," "lower," "horizontal," "vertical," "left," "right," "over," "on," "near," and the like. These terms are used, where applicable, to provide some clarity of description when dealing with relative relationships. But, these terms are not intended to imply absolute relationships, positions, and/or orientations.

As used in this disclosure, "automatically" means that an act can occur after a previous act without the need to receive additional user input before initiating performance of the act.

As used in the disclosure, "application" includes programs implemented with computer-executable instructions executable by a mobile device, as well as programs where some or all of the application functionality is accessed over a network, for example, network applications or web applications.

The invention makes reference to machine learning models and machine learning data sets. What is meant by a machine learning model is one of a learning-based decision model which uses a machine learning algorithm, such as AdaBoost, which evaluates inputs based on a model trained on past inputs to predict the user response. Thus, when using a machine learning based model as disclosed herein, the digital image, such as digital images of the reference diagnostic devices, is fed back to the decision model to update the learning. The behavior measurement can be additionally uploaded to a server for aggregate learning of the user behavior.

More sophisticated super-resolution algorithms may be used in this invention typically leverage machine learning techniques. Among them are sparse-representation, Kernel Ridge Regression (KRR), anchored neighbor regression (ANR), and in-place example regression.

In addition, it is well known that dedicated processing resources, such as graphical processing units, may be provided as various implementation forms, wherein the graphics processing units are a typical example of dedicated processing resources. In the present disclosure, to illustrate specific examples in detail, graphics processing units are taken as an example for describing the technical solution. However, such illustration is merely exemplary, and the technical solution of the present disclosure may be applicable to any dedicated processing resources rather than being limited to graphics processing units.

The processors describe in this invention may encompass a machine learning engine, and the databases described herein may have instructions that direct and/or cause the dynamic training response output generated machine learning model. The instructions included in one or more databases include herein provides the instructions to enable dynamic training response output generation control and to set, define, and/or iteratively refine optimization rules and/or other parameters used by the dynamic training response output generation control platform.

Figure 1:
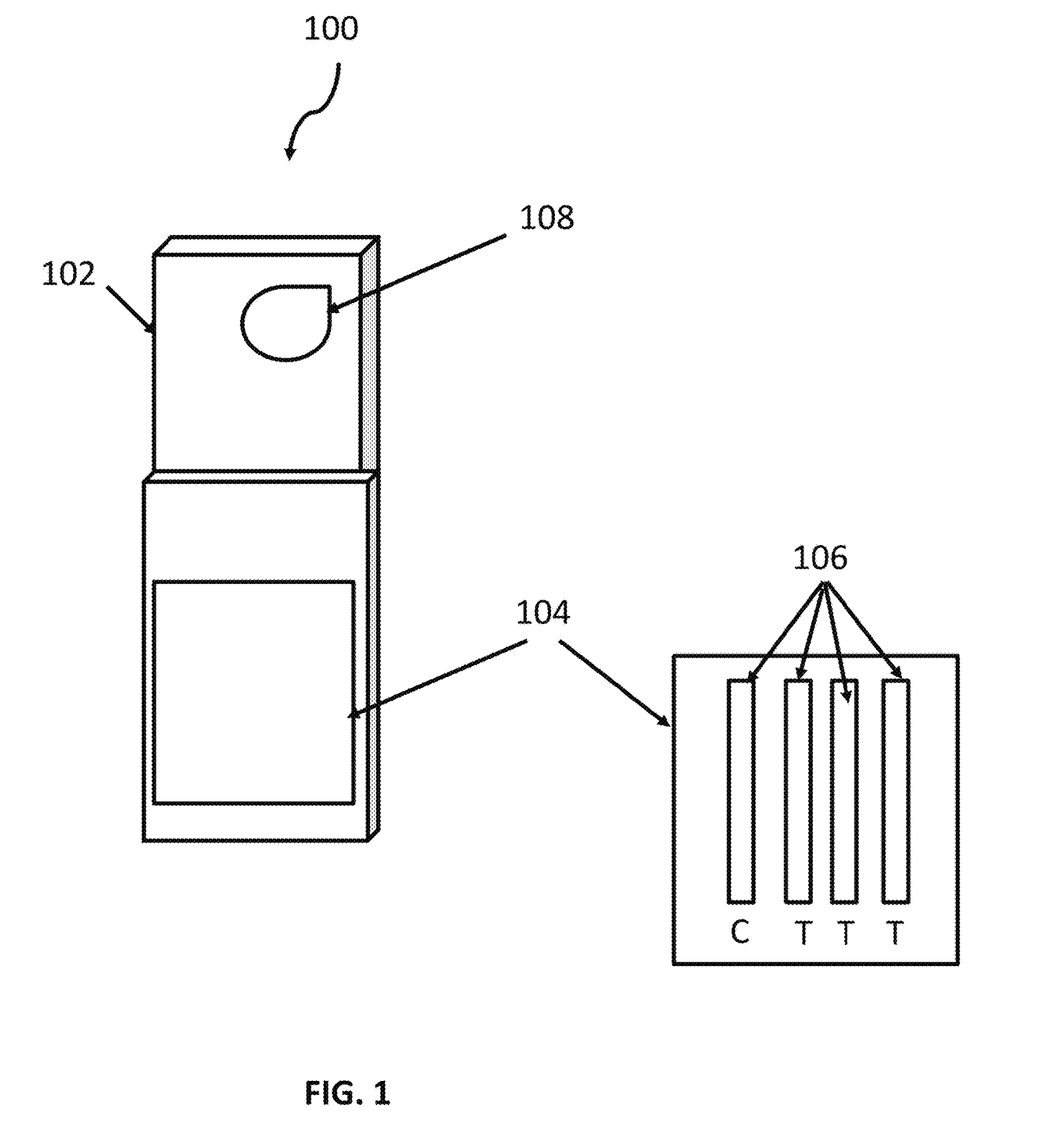
FIG. 1 is an exemplary depiction of a diagnostic device that may be used with the present invention.

FIG. 1 is an exemplary depiction of a diagnostic device 100 that may be used with this invention. While diagnostic device 100 is depicted as a drug dipstick, the present invention contemplates using a urine cup, saliva stick, or any similar diagnostic device for use in analyzing the analytes in a biological sample. Diagnostic device 100 may include a housing 102 for including a drug panel 104, therewith. In one exemplary embodiment, drug panel 104 is included on the face of housing 102. In another exemplary embodiment, drug panel 104 may contained within housing.

Additionally, diagnostic device 100 may include a diagnostic device identifier 108. Diagnostic device identifier 108 may be useful for identifying the manufacture, manufacturer part number, stockkeeping unit, bar code, QR code or the like. Further still, while the present invention describes the diagnostic device identifier 108 as being encrypted, the diagnostic device identifier 108 may be unencrypted when including with housing 102.

Drug panel 104 is configured to come in contact with a biological sample, such as, saliva, urine, blood, or the like when used. Drug panel 104 include one or more test strips 106. Test strips 106 of the conventional type ordinarily used to collect biological samples. Test strips 106 may include both T-Lines, for use in testing the presence of a drug, and C-Lines for use in verifying the validity of the test results.

Figure 2:
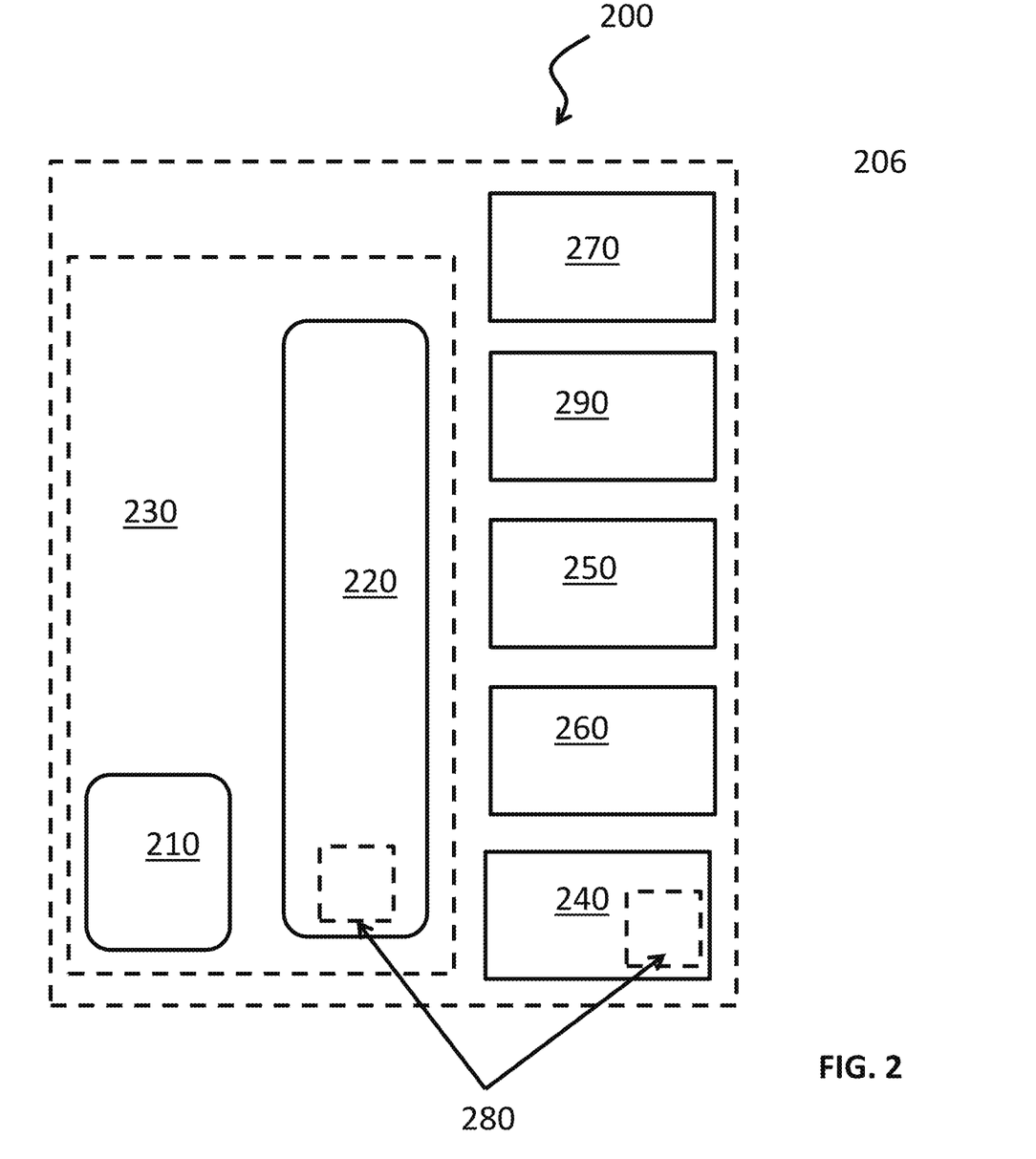
FIG. 2 is an exemplary depiction of a mobile device (e.g., smart phone) that may be used with the present invention.

FIG. 2 illustrates a generalized example of a suitable computing environment, mobile device 200, in which described embodiments, techniques, and technologies may be implemented. For example, the mobile device 300 is configured to implement the functionality for generating and transmitting context data, application metadata, and network addresses and computer-executable instructions for applications, as described herein. The mobile device 200 is not intended to suggest any limitation as to scope of use or functionality of the technology, as the technology may be implemented in diverse general-purpose or special-purpose computing environments. The disclosed technology may be implemented with other any hand-held devices, which includes multiprocessor systems, microprocessor-based or programmable consumer electronics, network PCs, minicomputers, and the like. Mobile device 200 may be, for example, a smart phone, iPad, smart pad, or the like.

With reference to FIG. 2, hand-held mobile device 200 includes at least one central processing unit 210 and memory 220. In FIG. 2, this most basic configuration of mobile device 200 is included within a dashed line. The central processing unit 210 executes computer-executable instructions and may be a real or a virtual processor. In a multi-processing system, multiple processing units execute computer-executable instructions to increase processing power and as such, multiple processors can be running simultaneously. The memory 220 may be volatile memory (e.g., registers, cache, RAM), non-volatile memory (e.g., ROM, EEPROM, flash memory, etc.), or some combination of the two. The memory 220 stores software 280 that can, for example, implement the technologies described herein.

Mobile device 200 may have additional features. For example, mobile device 300 includes storage 240. Mobile device 200 may further in, one or more output devices 260, such as, a computer screen or output ports. Mobile device 200 may further include a machine learning engine 290, for performing a machine learning algorithm. Mobile device 200 may further include a digital camera 270 for capturing a digital image of a subject. An interconnection mechanism (not shown) such as a bus, a controller, or a network, interconnects the components of the mobile device 200. Typically, operating system software (not shown) provides an operating environment for other software executing in the mobile device 200, and coordinates activities of the components of the mobile device 200.

The storage 240 may be a removable or non-removable memory, and may include flash memory, CD-ROMs, CD-RWs, DVDs, or any other non-transitory storage medium which can be used to store information and that can be accessed within the computing environment 200. The storage 240 stores instructions for the software 280, which can implement technologies described herein.

Mobile device 200 may include input device(s) 250 may be a touch input device, such as a keyboard, keypad, mouse, pen, or trackball, a voice input device, a scanning device, proximity sensor, image-capture device, or another device, that provides input to the computing environment 300. For audio, the input device(s) 250 may be a sound card or similar device that accepts audio input in analog or digital form, or a CD-ROM reader that provides audio samples to the mobile device 200. The output device(s) 260 may be a display, printer, speaker, CD-writer, or another device that provides output from the mobile device 200.

Computer-readable media are any available media that can be accessed within a mobile device 200. By way of example, and not limitation, with the mobile device 300, computer-readable media include memory 220 and/or storage 240. As should be readily understood, the term computer-readable storage media includes non-transitory storage media for data storage such as memory 220 and storage 240, and not transmission media such as modulated data signals.

Figure 3:
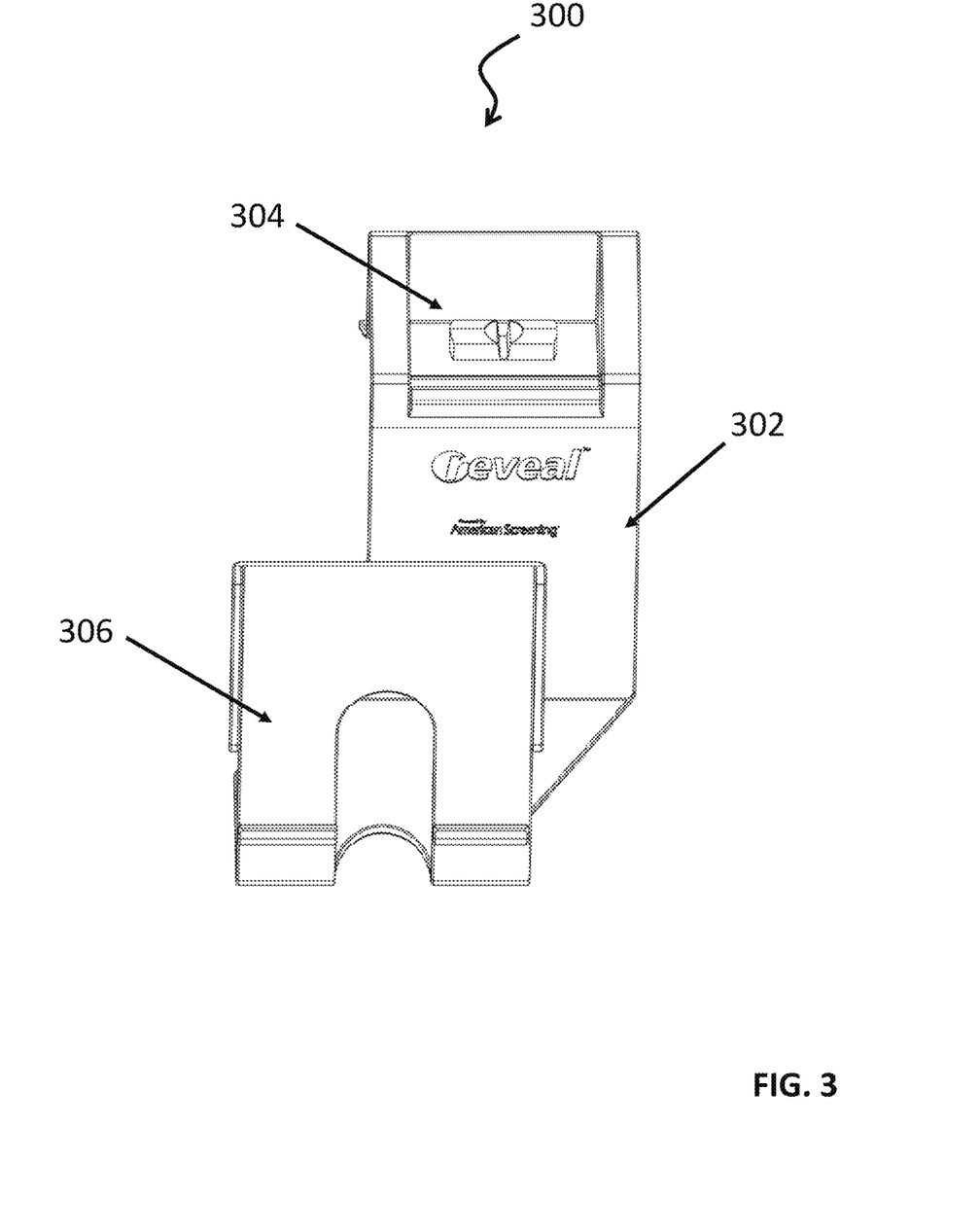
FIG. 3 is an exemplary is an exemplary diagnostic tabletop stand that may be used with the present invention.

FIG. 3 shows an exemplary drug testing stand 300 that may be used with the present invention. Stand 300 may be constructed of a rigid housing 302. As shown, stand 300 may include a front tray 306 for receiving mobile device 200, therein. (Shown in FIG. 4, below) Stand front tray 306 is constructed to receive mobile device 200 and hold mobile device 200 immobile therein. In one embodiment, tray 306 may hold mobile device 200 removably fixed thereon.

Housing 302 may further include a stand compartment 304 for receiving a diagnostic device 100. (Shown in FIG. 4). Compartment 304 may be configured to hold diagnostic device 100 immovably. Compartment 304 may removably hold diagnostic device 100, therein. A suitable stand 300 for use with this invention is described in U.S. Provisional Application No. 62/948,260, which is incorporated herein by reference.

Figure 4:
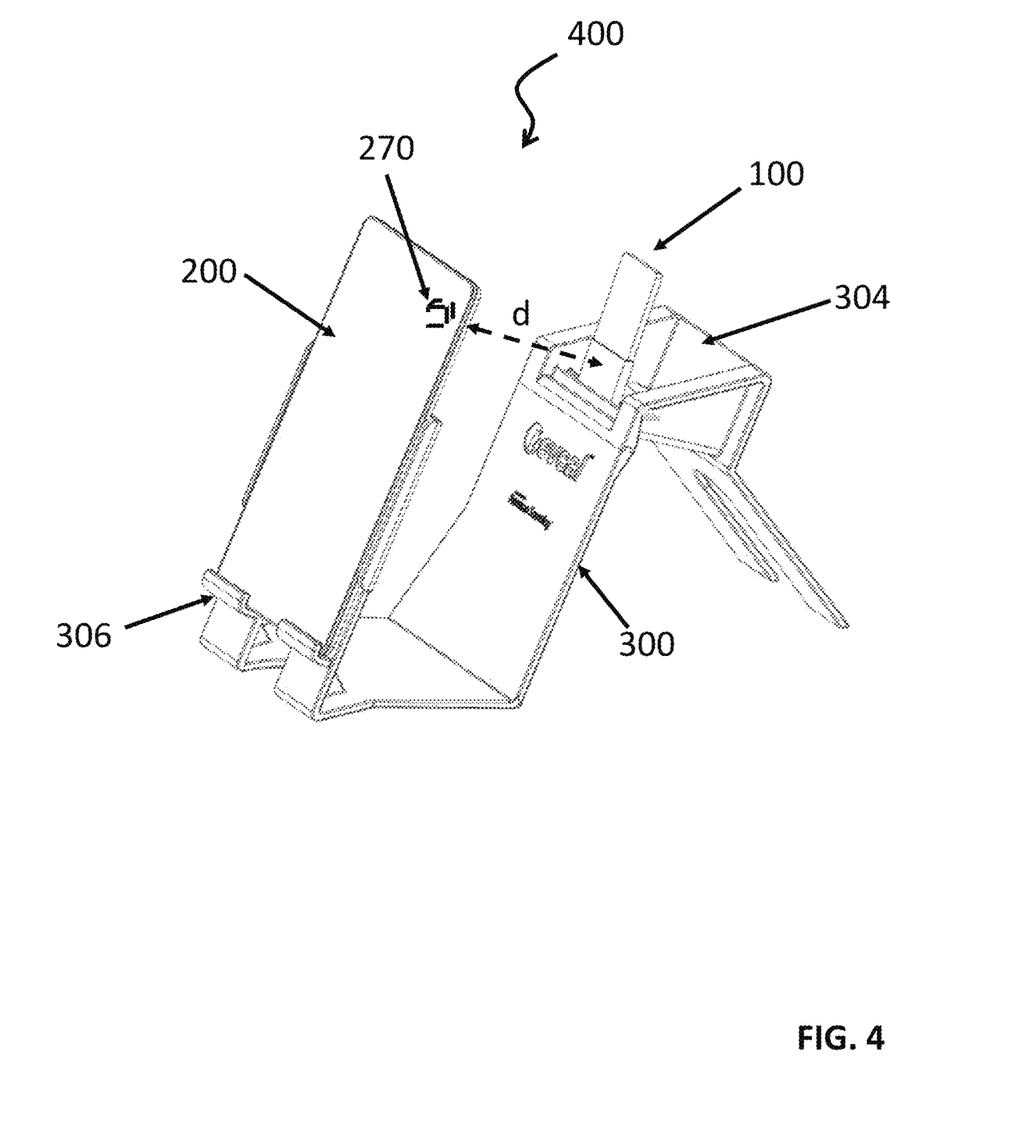
FIG. 4 is a example of a system for using the diagnostic method according to various embodiments of the present invention.

FIG. 4 is an exemplary embodiment of the present invention showing the diagnostic device 100, and the mobile device 200 removably affixed to stand 300. As is shown, diagnostic device 100 is removably affixed to compartment 304, and mobile device 200 is removably affixed to front tray 306. In preferred embodiment, stand 300 is configured hold mobile device 200 at a fixed distance, d, from diagnostic device 100. In one embodiment, stand 300 is configured hold mobile device 200 at a fixed distance, d, from the focal point of digital camera 270.

Figure 5:
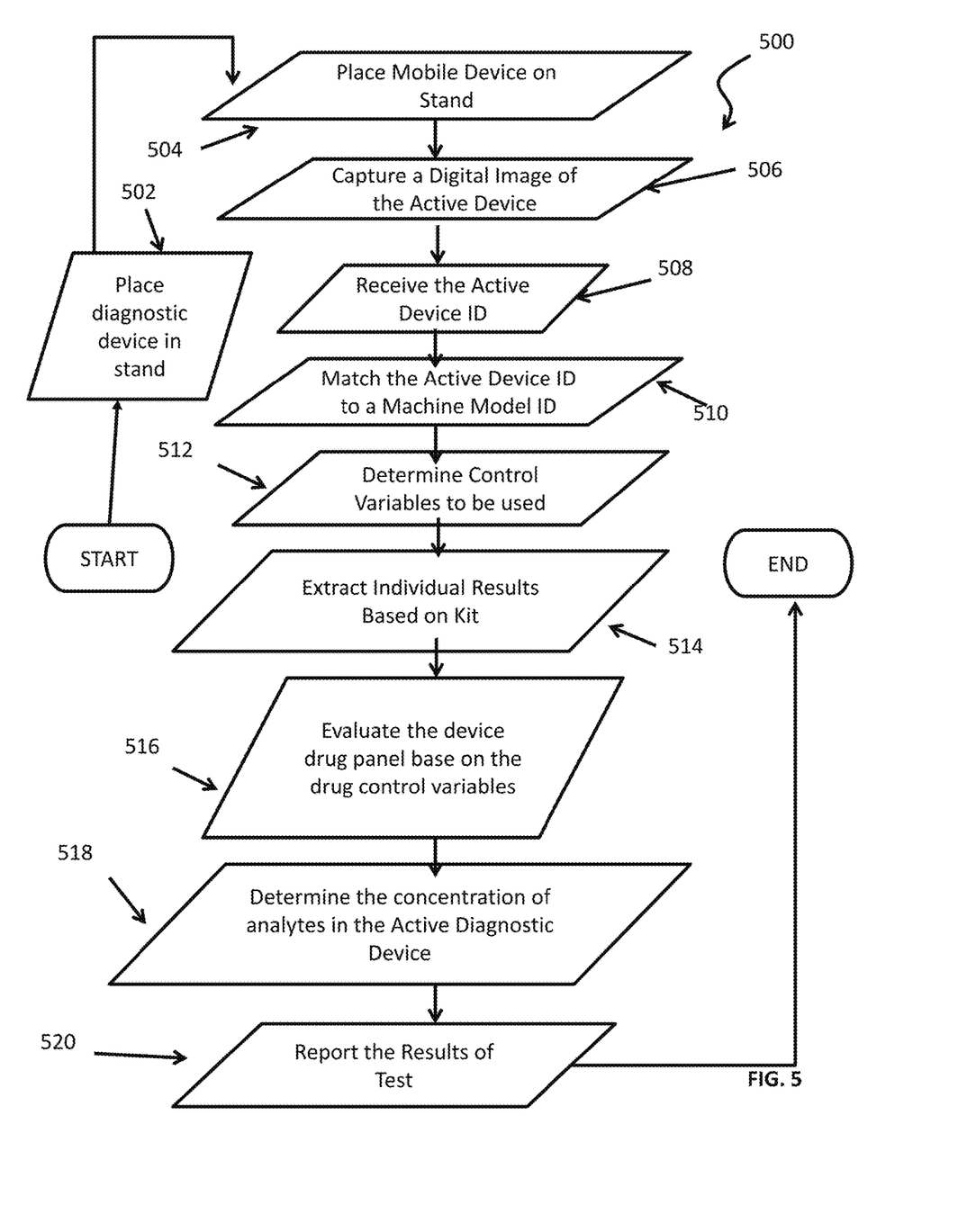
FIG. 5 is another typical example of a method for evaluating a diagnostic device that is practiced according to the invention.

FIG. 5 depicts an exemplary method 500 for determining the concentration of analytes in a biological sample using a machine learning algorithm. To prepare the diagnostic device 100 for processing, diagnostic device 100 is placed in contact with a biological sample as is done in conventional drug testing. For each is understanding, a diagnostic device 100 that has been placed in contact with a biological sample in preparation for reading is called an "active diagnostic device."

According to the method shown, an active diagnostic device 100 is placed on stand 200 (Step 502) in compartment 304. Additionally, mobile device 200 may be placed on a stand 300 (Step 504) in tray 306. The user may take a digital image of the drug test strip 100 using the mobile device 200 (Step 506). The drug test strip 100 may be placed in the camera optical focal point 270. That is, drug test strip 100 may be located on stand 300 such that the camera may With brief reference to FIG. 6, a method for generating a database of machine learning models, is prepared using a machine learning algorithm which uses a plurality of digital images of diagnostic devices as the data set for the algorithm. The plurality of digital images of diagnostic devices that are provided to the machine learning algorithm may pre-recorded images of diagnostic devices showing the diagnostic device identifier 108, and drug panel 104. As used herein, the diagnostic devices shown in the pre-recorded digital images are called "reference diagnostic devices." Consequently, the output of the machine learning algorithm is called a "machine learning model of diagnostic devices," herein.

Figure 6:
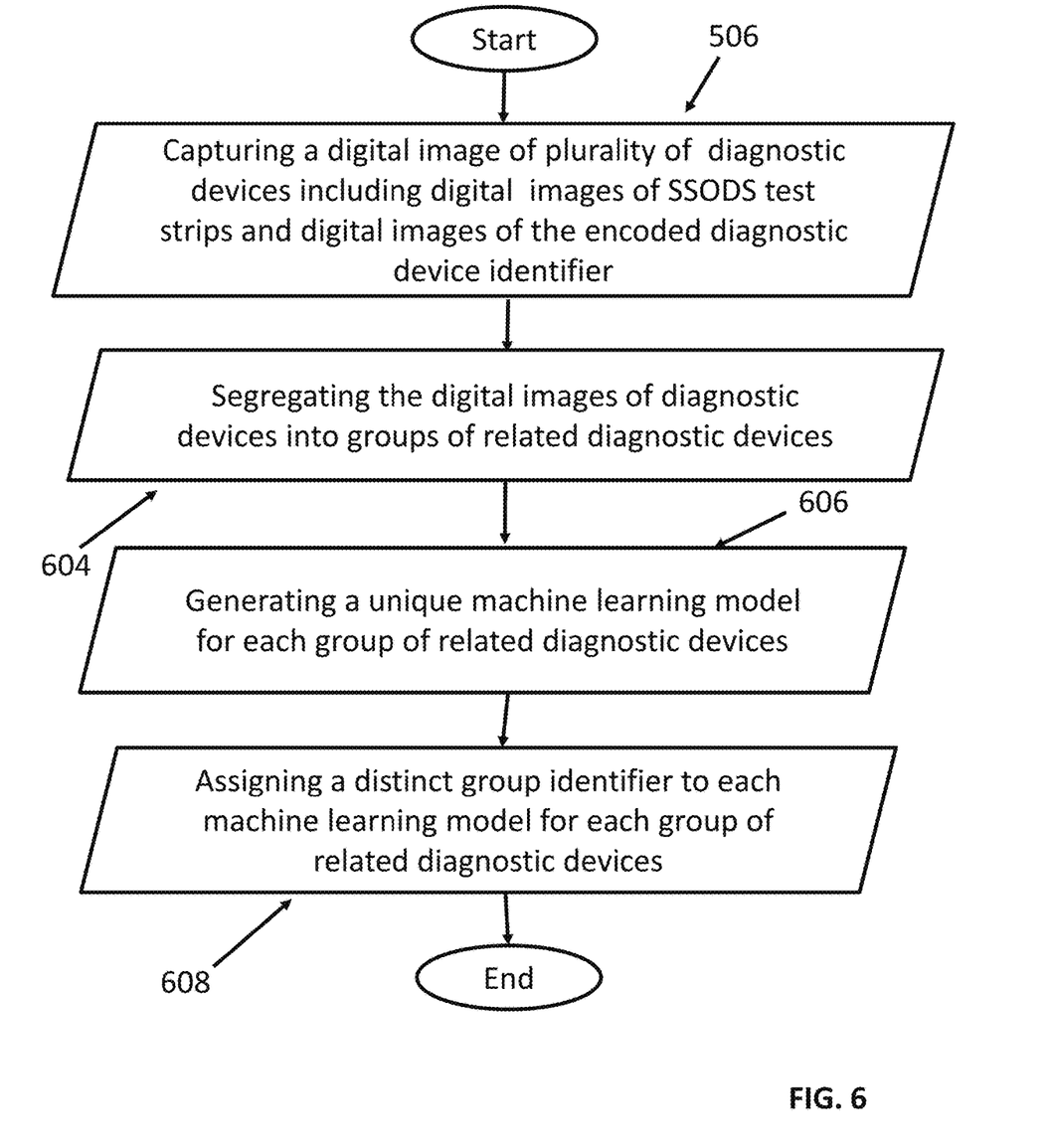
FIG. 6 is an exemplary method for generating a database of machine learning models which use a plurality of reference diagnostic devices as the machine learning data set.

In a preferred embodiment, a plurality of digital images of the referenced diagnostic devices are separated into a group of related diagnostic devices. (Step 604) In one particular embodiment, related diagnostic devices may be diagnostic devices that share a manufacture, stock keeping unit number, QR code, or bar code. In this way, the groups that are formed are groups of related reference diagnostic device.

In accordance with this invention, the machine learning model database is constructed by providing the machine learning algorithm with a plurality of digital images of diagnostic devices of that are related. More particularly, the machine learning algorithm is provided groups of related diagnostic devices. As such, the resulting machine learning models generated by the machine learning algorithm represents a distinct machine learning model for each unique group of related diagnostic devices. (Step 606) Each distinct machine learning model of diagnostic devices is provided with a distinct group identifier for use in recalling the machine learning model from memory 220. (Step 608) According to various embodiments of the invention, the machine learning algorithm may be stored in memory 220 and accessed by processor 210.

With return reference to FIG. 5, as noted, diagnostic devices 100 may include a unique diagnostic device identifier 108, whether encrypted or unencrypted. In this case, diagnostic device identifier 108 may be used to identify whether the diagnostic device 100 is related to at least any one other of the diagnostic devices comprising the machine learning models of diagnostic devices. The diagnostic device identifier 106 provides information to the mobile device processor 210 concerning the identity of the diagnostic device. A digital image of the identifier 106 is captured by digital camera optical focal point 270 and provided to processor 220. Processor 220 may receive the diagnostic device identifier 106 (Sep 508) and compare (i.e. "match") the diagnostic device identifier 106 to a distinct group identifier for at least one of the machine learning models for each group of related diagnostic devices discussed in Step 608 above (Step 510). If a match is made, the diagnostic device identifier may be considered valid. By valid what is meant is that the diagnostic device that is identified is one capable of being evaluated according to the method of this invention.

More specifically, if a match is made, then the diagnostic device 100 may be evaluated by the methods of the present invention. That is, a diagnostic device 100 is valid if the methods of this invention can determine the concentration of analytes contained in its drug panel. That is, in one embodiment of the invention, mobile device 200 may capture a digital image of the diagnostic device 100 including the diagnostic device identifier 109, and provide the digital image to the processor 210. Processor 210 may access memory 220 to retrieve identifying information unique identifier for the machine learning model of the diagnostic device stored therein. (Step 508) Processor 210 matches the diagnostic device identifier 109 to at least one identifier for at least one of the stored unique machine learning model of diagnostic devices. (Step 510) The matched identifier for the at least one of the stored unique machine learning models of diagnostic devices is used to determine which control variables are to be used to determine the concentration of analytes in the diagnostic device drug panel 104. (Step 512)

In accordance with the invention, a data base of machine learning models of drug panels 104 is generated for use in evaluating the concentration of analytes contained in the drug panel of an active diagnostic device. As noted, drug panels 104 include test strips 106, which absorb the biological fluid to be tested. The method according to this invention evaluates the drug test strips 106 to determine the concentration of analytes present.

The present invention compares an image of the drug test strips 106 for an active diagnostic device 100 to a machine learning model of drug panel 104. As described more fully below, the drug panel 104 may be segregated into grid having a plurality of modules, wherein at least one module includes a drug control variable that can be used to evaluate the concentration of analytes in drug panel 104.514 To evaluate the concentration level of analytes absorbed by the drug test strips 106, a database of machine learning models of drug panels is generated.

Figure 7:
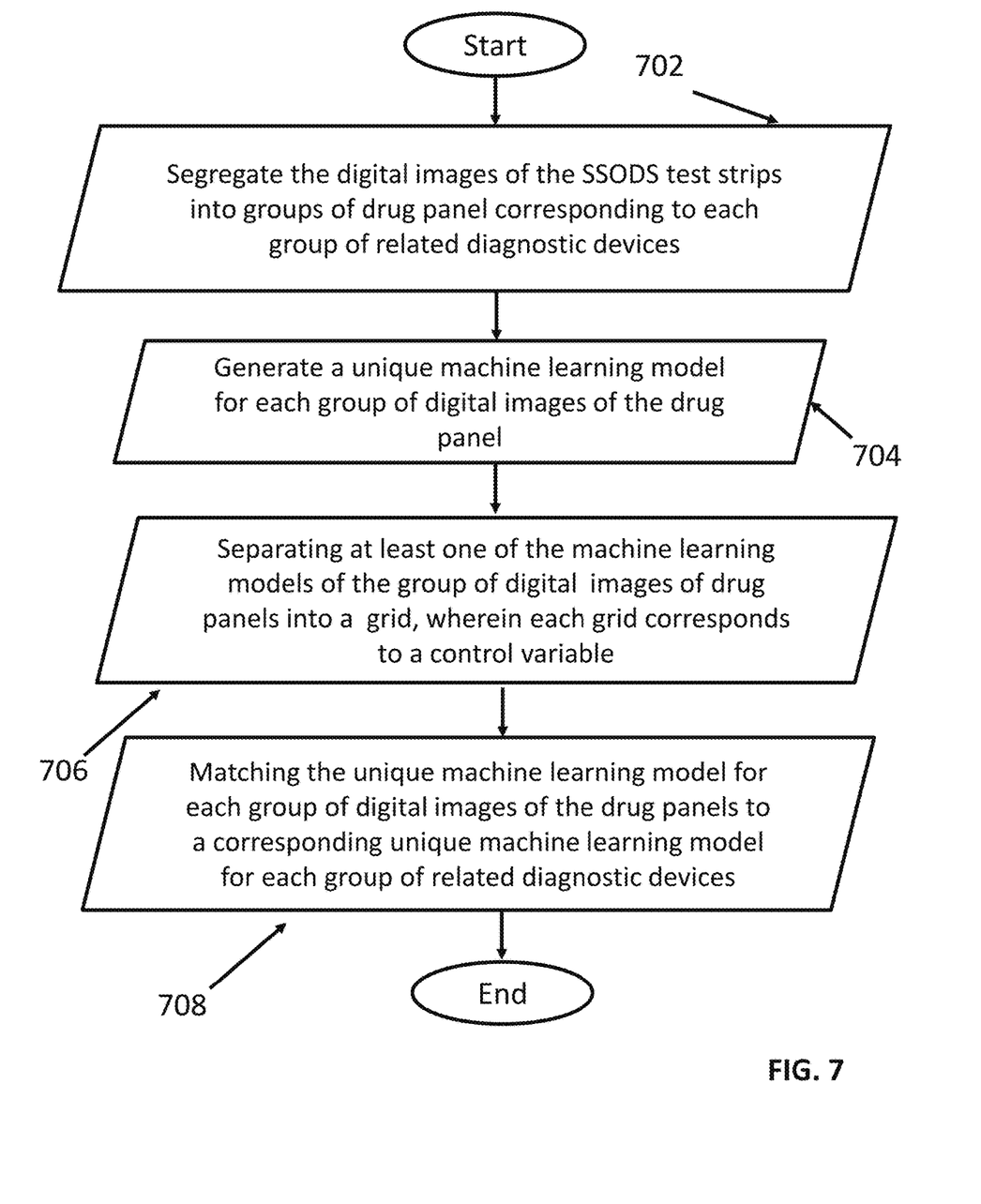
FIG. 7 is an exemplary method for generating a database of machine learning models which use a plurality of reference SSODS test strips as the machine learning data set, and generating test control variables.

With reference to FIG. 7, pre-recorded digital images of drug panels 104 containing drug test strips 106 is provided to a machine learning algorithm, such as is described above. In a preferred embodiment, the plurality of pre-recorded test strips 104 include multiple test strips 106, which show differing concentration level of analytes. For example, the test strips 104 may indicate different levels of concentrations by indicating different intensities of color corresponding to the concentration level. Therefore, the data set of test strips 104 used to generate the machine learning models of the drug panels includes drug test strips 104 having different shades and intensities of colors representing the concentration of analytes.

Pre-recorded digital images of related diagnostic devices drug panels 104 are grouped together (Step 702) and used as data sets for the machine learning algorithm to generate the database of the machine learning models of drug panels. (Step 704). In one embodiment, a plurality of pre-recorded digital images of test strips 106 that indicate the same level of concentration to within a predetermined tolerance are grouped together. For example, the image of drug test strips 104 of related diagnostic devices 100, which indicate the same concentration of analytes (i.e., X %) to within a tolerance of 0.01% may be grouped and used a data set for a machine learning algorithm to produce a machine learning model of a drug test strips indicating a concentration of X %.

The ensure increase accuracy of the analysis, the machine learning models of the drug test strips 104, the machine learning model of drug panels is separated into a grid, wherein each module of the grid includes a control variable used to evaluate the drug panel 104 of an active diagnostic device 100. (Step 706). The control variables may include a portion of machine learning model of a test strip 104 contained in the grid. In another embodiment, the control variables may be stored in a database in memory 220. In another embodiment, the control variable may be stored in memory 220 and correlated to the modules of the machine learning model of drug panel grids.

In another exemplary embodiment, a unique machine learning model of drug panels identifier is assigned to each machine learning model of drug panels. Once the processor determines the desired machine learning model of diagnostic devices that matches the active diagnostic device, then processor 210 selects the corresponding machine model of drug panels to be used to evaluate the concentration of analytes in the active diagnostic device drug panel. (Step 708)

With return reference to FIG. 8, a digital image of the active diagnostic device drug panel 104 (and drug test strips 106) must be prepared to be compared to the selected machine learning model of drug panels having the control variables. As such, an image of the active diagnostic device drug panel 104 is captured by digital camera 270 and provided to processor 210. Processor 210 then separates the image of the active drug panel 104 into a grid of images. (Step 804)

Figure 8:
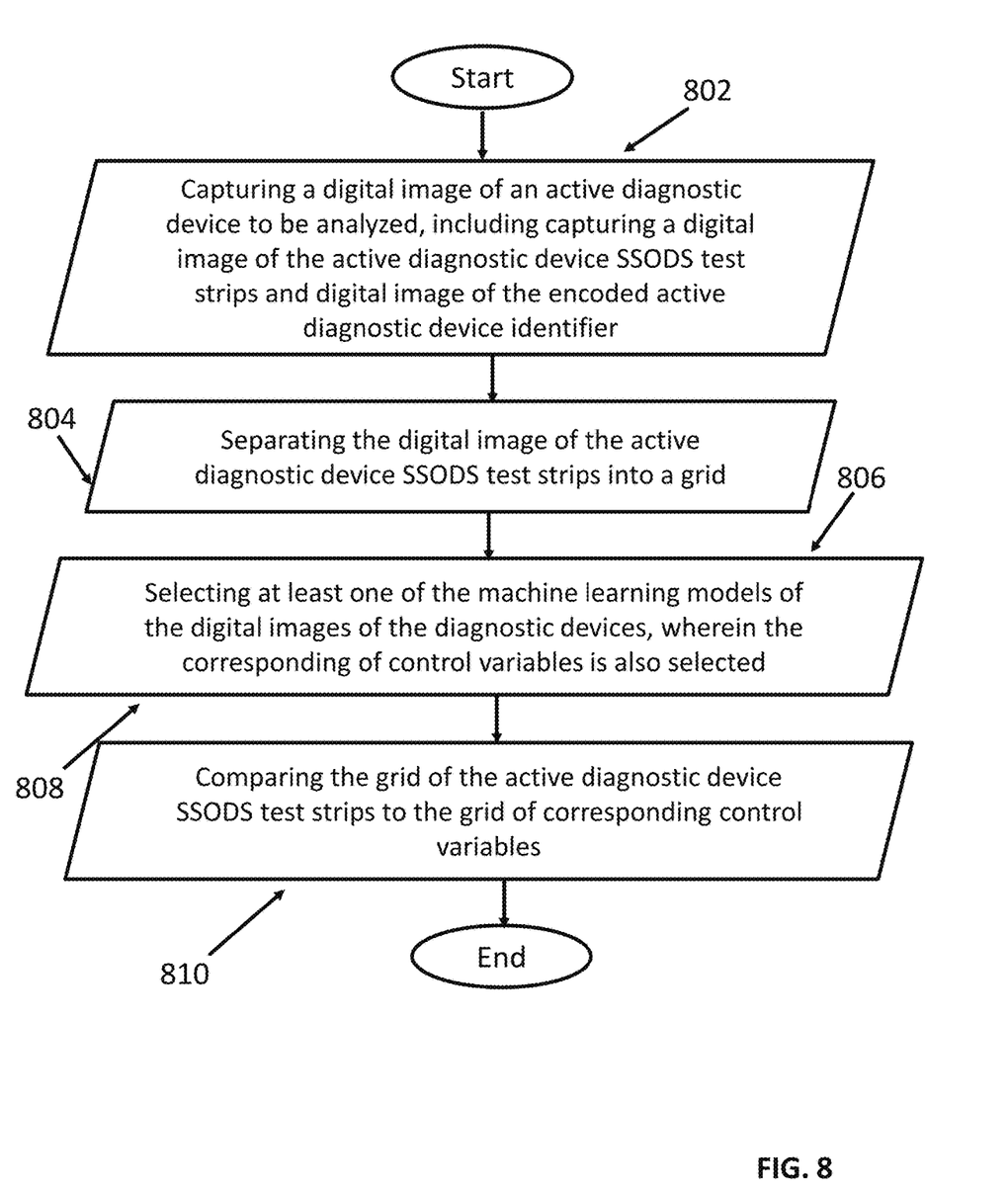
FIG. 8 is an exemplary method for evaluating a diagnostic device according to the present invention.

Processor 210 may select at least one of the machine learning model of drug panels 104 for comparing to the drug panel 104 of the active diagnostic device 100. Processor 210 may select the desired machine learning model of drug panels 104 by based on the machine learning models of diagnostic devices 100. (Step 808) Processor 210 may then compare corresponding modules of the active diagnostic device drug panel 104 grid to corresponding grid modules of the machine learning model drug panel containing control variable. (Step 810)

With return reference to FIG. 5, processor 210 may map at least one of the modules of the grid of the active diagnostic device drug panels 104 to the drug control variables used to evaluate the concentration of analytes in drug panel 104 on a grid-by-grid basis. (Step 516) In accordance with the invention, in one particular embodiment the present invention may be configured to interpret the semi-quantitative result of the test based on the comparison of the images of the machine language generated data. For example, the drug test strip may be configured to indicate the concentration of the drug present by correlating the concentration to the intensity of the color shown on the T Line. Test results for semi-quantitative tests may be reported as trace amount; 1+, 2+, or 3+; or positive at 1:160 (titer or dilution).

(Step 518) The semi-quantitative results would be a range based on the cutoff level which could detect semi-quantitative values-50% below all the way up to 2× time the concentration value with line intensity or pantone color. The results of the semi-quantitative analysis of an active diagnostic device may be reported to output devices 260. (Step 520)

The disclosed methods, apparatus, and systems should not be construed as limiting in any way. Instead, the present disclosure is directed toward all novel and nonobvious features and aspects of the various disclosed embodiments, alone and in various combinations and sub-combinations with one another. The disclosed methods, apparatus, and systems are not limited to any specific aspect or feature or combination thereof, nor do the disclosed embodiments require that any one or more specific advantages be present or problems be solved. The techniques and solutions described in this application can be used in various combinations to provide a better user experience with mobile devices, including mobile devices such as smartphones.

Any of the methods described herein can be performed via one or more computer-readable media (e.g., storage or other tangible media) comprising (e.g., having or storing) computer-executable instructions for performing (e.g., causing a computing device to perform) such methods. Operation can be fully automatic, semi-automatic, or involve manual intervention.

It will be recognized that the various embodiments can be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of embodiments shown in software may be implemented in hardware and vice versa.

In view of the many possible embodiments to which the principles of the disclosed invention may be applied, it should be recognized that the illustrated embodiments are only preferred examples of the invention and should not be taken as limiting the scope of the invention.

I claim:

1. A computer implemented method for evaluating one of a plurality of unique diagnostic devices, the method comprising:
   a. capturing a digital image of each one of the plurality of unique diagnostic devices to produce a corresponding unique digital image for each one of the plurality of unique diagnostic devices, wherein each one of the plurality of unique diagnostic devices includes a plurality of spatially separated optically detectable signal (SSODS) test strips, and wherein each one of the plurality of unique diagnostic devices includes an encoded identifier, wherein capturing a digital image of each one of the plurality of unique diagnostic devices includes taking a digital image of the each one of the plurality of spatially separated optically detectable signal test strips to produce corresponding unique digital image of each one of the plurality of spatially separated optically detectable signal test strips,
   b. grouping the plurality of unique digital images of the plurality of unique diagnostic devices to generate a plurality of groups of unique digital images of the unique diagnostic devices, wherein each group of digital images of unique diagnostic devices is limited to related diagnostic devices, c. generating a unique machine learning model for each group of digital images of unique diagnostic devices,
d. assigning a distinct machine learning model group identifier for each unique machine learning model for each group of digital images of unique diagnostic devices,
e. generating a plurality of groups of digital images of the plurality of spatially separated optically detectable signal test strips, wherein each group of digital images of spatially separated optically detectable signal test strips is limited to the related diagnostic devices,
f. generating a unique machine learning model for each group of digital images of spatially separated optically detectable signal test strips,
g. separating each unique machine learning model for each group of digital images of spatially separated optically detectable signal test strips into a grid including a plurality of modules,
h. assigning a drug control variable to at least one module of the modules of the unique machine learning model for each group of digital images of spatially separated optically detectable signal test strips,
i. using a camera enabled device to capture a digital image of an active diagnostic device, wherein the active diagnostic device is of similar construction to at least one of the plurality of unique diagnostic devices, wherein the active diagnostic device includes a unique active diagnostic device identifier, wherein the active diagnostic device includes multiple spatially separated optically detectable signal test strips,
j. capturing a digital image of the active diagnostic device multiple spatially separated optically detectable signal test strips, wherein a portion of the digital image of the active diagnostic device includes a digital image of the active diagnostic device multiple spatially separated optically detectable signal test strips, and wherein the digital image of the active diagnostic device multiple spatially separated optically detectable signal test strips represents a visual concentration of the analytes,
k. selecting at least one of the unique machine learning models for at least one of the groups of digital images of unique diagnostic devices by matching the active diagnostic device identifier to at least one of the distinct machine learning model group identifiers,
l. separating the digital image of the active diagnostic device multiple spatially separated optically detectable signal test strips into a grid having a plurality of modules, wherein at least one module of the grid of the digital image of the active diagnostic device multiple spatially separated optical detectable signal test strips is a digital representation of at least a portion of each at least one of the active diagnostic device multiple spatially separated optically detectable signal test strips, and
m. comparing at least one module of the digital image of the active diagnostic device multiple spatially separated optically detectable signal test strips to at least one of the modules the unique machine learning model for each group of digital images of spatially separated optically detectable signal test strips to determine the concentration of analytes in the active diagnostic device, wherein comparing the at least one module of the drug control variable to at least one module of the modules of at least one of the unique machine learning model for each group of digital images of spatially separated optically detectable signal test strips includes evaluating the assigned drug control variable of at least one of the at least one module of the grid modules of the unique machine learning model for each group of digital images of spatially separated optically detectable signal test strips to determine the concentration of analytes in the active diagnostic device.

2. A computer implemented method for evaluating one of a plurality of unique diagnostic devices, the method comprising:
a. capturing a digital image of each one of the plurality of unique diagnostic devices to produce a corresponding unique digital image for each one of the plurality of unique diagnostic devices, wherein each one of the plurality of unique diagnostic devices includes a plurality of spatially separated optically detectable signal (SSODS) test strips, and wherein each one of the plurality of unique diagnostic devices includes a diagnostic device identifier, wherein capturing a digital image of each one of the plurality of unique diagnostic devices includes taking a digital image of the each one of the plurality of spatially separated optically detectable signal test strips to produce corresponding unique digital image of each one of the plurality of spatially separated optically detectable signal test strips,
b. grouping the plurality of unique digital images of the plurality of unique diagnostic devices to generate a plurality of groups of unique digital images of the unique diagnostic devices, wherein each group of digital images of unique diagnostic devices is limited to related diagnostic devices,
c. generating a unique machine learning model for each group of digital images of unique diagnostic devices,
d. assigning a distinct machine learning model group identifier for each unique machine learning model for each group of digital images of unique diagnostic devices,
e. generating a plurality of groups of digital images of the plurality of spatially separated optically detectable signal test strips, wherein each group of digital images of spatially separated optically detectable signal test strips is limited to related diagnostic devices,
f. generating a unique machine learning model for each group of digital images of spatially separated optically detectable signal test strips,
g. separating each unique machine learning model for each group of digital images of spatially separated optically detectable signal test strips into a predetermined grid, wherein each grid represents a specific drug control variable,
h. using a camera enabled device to capture a digital image of an active diagnostic device, wherein the active diagnostic device is of similar construction to at least one of the plurality of unique diagnostic devices, wherein the active diagnostic device to be read includes a unique active diagnostic device encoded identifier, wherein the active diagnostic device includes multiple spatially separated optically detectable signal test strips,
i. capturing a digital image of the active diagnostic device multiple spatially separated optically detectable signal test strips, wherein a portion of the digital image of the active diagnostic device includes a digital image of the active diagnostic device multiple spatially separated optically detectable signal test strips,
j. selecting at least one of the unique machine learning models for at least one of the groups of digital images of unique diagnostic devices by matching the encoded active diagnostic device identifier to at least one of the distinct machine learning model group identifiers, k. separating the digital image of the active diagnostic device multiple spatially separated optically detectable signal test trips into a grid, wherein each module of the multiple spatially separated optical detectable signal test strips grid is a digital representation of at least a portion of each one of the multiple spatially separated optically detectable signal test strips, and l. comparing at least one module of the digital image of the active diagnostic device multiple spatially separated optically detectable signal test strips to at least one of the modules of grids including specific drug control variables to determine the concentration of analytes in at least one of the active diagnostic device multiple spatially separated optically detectable test strips.

3. A computer implemented method for evaluating one of a plurality of unique diagnostic devices, the method comprising:

a. capturing a digital image of each one of the plurality of unique diagnostic devices to produce a corresponding unique digital image for each one of the plurality of unique diagnostic devices, wherein each one of the plurality of unique diagnostic devices includes a drug panel, and wherein each one of the plurality of unique diagnostic devices includes an encoded identifier, wherein capturing a digital image of each one of the plurality of unique diagnostic devices includes taking a digital image of the drug panels to produce corresponding unique digital image of each one of the plurality of spatially separated optically detectable signal test strips, b. grouping the plurality of unique digital images of the plurality of unique diagnostic devices to generate a plurality of groups of unique digital images of the unique diagnostic devices, wherein each group of digital images of unique diagnostic devices is limited to related diagnostic devices, c. generating a unique machine learning model for each group of digital images of unique diagnostic devices, d. assigning a distinct machine learning model group identifier for each unique machine learning model for each group of digital images of unique diagnostic devices, e. generating a plurality of groups of digital images of the drug panels, wherein each group of digital images of the drug panels is limited to related diagnostic devices, f. generating a unique machine learning model for each group of the drug panels, g. separating each unique machine learning model for each group of digital images of drug panels into a grid, wherein each module of the grid represents a specific drug control variable, h. using a camera enabled device to capture a digital image of an active diagnostic device to be read, wherein the active diagnostic device to be read is of similar construction to the plurality of unique diagnostic devices, wherein the active diagnostic device to be read includes a unique active diagnostic device encoded identifier, wherein the active diagnostic device includes multiple drug panels, i. capturing a digital image of the active diagnostic device multiple spatially separated optically detectable signal test strips, wherein a portion of the digital image of the active diagnostic device includes a digital image of the drug panels, j. decoding the active diagnostic device encoded identifier to receive a decoded active diagnostic device identifier, k. selecting at least one of the unique machine learning models for at least one of the groups of digital images of unique diagnostic devices by matching the decoded active diagnostic device identifier to at least one of the distinct machine learning model group identifiers, l. separating the digital image of the active diagnostic device drug panel, wherein each module of the active diagnostic device drug panel grid is a digital representation of at least a portion of each one of the drug panels, and m. comparing at least one module of the digital image of the active diagnostic device drug panel to at least one of the modules of grids of specific drug control variables to determine a concentration of analytes in at least one of the active diagnostic device multiple spatially separated optically detectable test strips.

* * * * *